United States Patent [19]

Jian

[11] Patent Number: 5,398,084
[45] Date of Patent: Mar. 14, 1995

[54] APPARATUS FOR MEASURING THE SPHERICAL SURFACE OF THE CORNEA

[76] Inventor: Jeen-hon Jian, 7/F., No. 8, Alley 33, Lane 90, Teh-Hsing E. Rd., Shih-Lin Dist., Taipei City, Taiwan, Prov. of China

[21] Appl. No.: 248,498

[22] Filed: May 24, 1994

[51] Int. Cl.$^6$ ............................................. A61B 3/10
[52] U.S. Cl. ..................................... 351/212; 351/247
[58] Field of Search ............... 351/205, 212, 247, 221, 351/211, 216

[56] References Cited

U.S. PATENT DOCUMENTS 4,660,947  4/1987  Amoils ................................. 351/247

*Primary Examiner*—William L. Sikes
*Assistant Examiner*—Huy Mai
*Attorney, Agent, or Firm*—Morton J. Rosenberg; David I. Klein

[57] ABSTRACT

An apparatus for measuring the spherical surface of the cornea including an annular mounting frame for fastening to the microscope barrel of a refracting unit, two contact metal springs concentrically fastened to the annular mounting frame at the bottom, a centering device suspended within the annular mounting frame to hold a light emitting diode at the center of the annular mounting frame, an annular light holder fastened to the annular mounting frame at the bottom to hold a series of light emitting diodes permitting them to be abutted against one another around a circle, and a lens grip fastened to the annular mounting frame at the bottom to hold down the annular light holder and having a lens on the inside for condensing the light of the light emitting diodes of the annular light holder into a ring of light for projecting onto the spherical surface of the cornea for measuring refraction of the eye.

1 Claim, 4 Drawing Sheets

APPARATUS FOR MEASURING THE SPHERICAL SURFACE OF THE CORNEA

BACKGROUND OF THE INVENTION

The present invention relates to an apparatus for measuring the spherical surface of the cornea.

Conventional apparatus for measuring the spherical surface of the cornea generally comprise a plurality of lamp bulbs fastened to a ring mount and arranged around a circle. When the lamp bulbs are turned on to give light, they project a ring of light onto the spherical surface of the cornea for measuring. This structure of cornea measuring apparatus is not safe in use because the lamp bulbs produce heat when they are turned on. Another drawback of this structure of cornea measuring apparatus is that the light rays from the lamp bulbs cannot be well condensed, thereby causing the ring of light diffused. Because the ring of light is formed by a series of circular spots of light but not a continuous line of light, it is difficult to achieve an accurate measuring.

SUMMARY OF THE INVENTION

The present invention has been accomplished to provide an apparatus for measuring the spherical surface of the cornea which eliminates the aforesaid drawbacks. According to the present invention, the apparatus comprises an annular mounting frame for fastening to the microscope barrel of a refracting unit, two contact metal springs concentrically fastened to the annular mounting frame at the bottom, a centering device suspended within the annular mounting frame to hold a light emitting diode at the center of the annular mounting frame, an annular light holder fastened to the annular mounting frame at the bottom to hold a series of light emitting diodes permitting them to be abutted against one another around a circle, and a lens grip fastened to the annular mounting frame at the bottom to hold down the annular light holder and having a lens on the inside for condensing the light of the light emitting diodes of the annular light holder into a ring of light for projecting onto the spherical surface of the cornea for measuring refraction of the eye. The lens grip and the annular light holder are respectively made from opaque material so that the light of the light emitting diodes on the annular light holder can be effectively condensed into a ring of light for projecting onto the spherical surface of the cornea.

DETAILED DESCRIPTION OF THE PREFERRED EMBODIMENT

Figure 1:
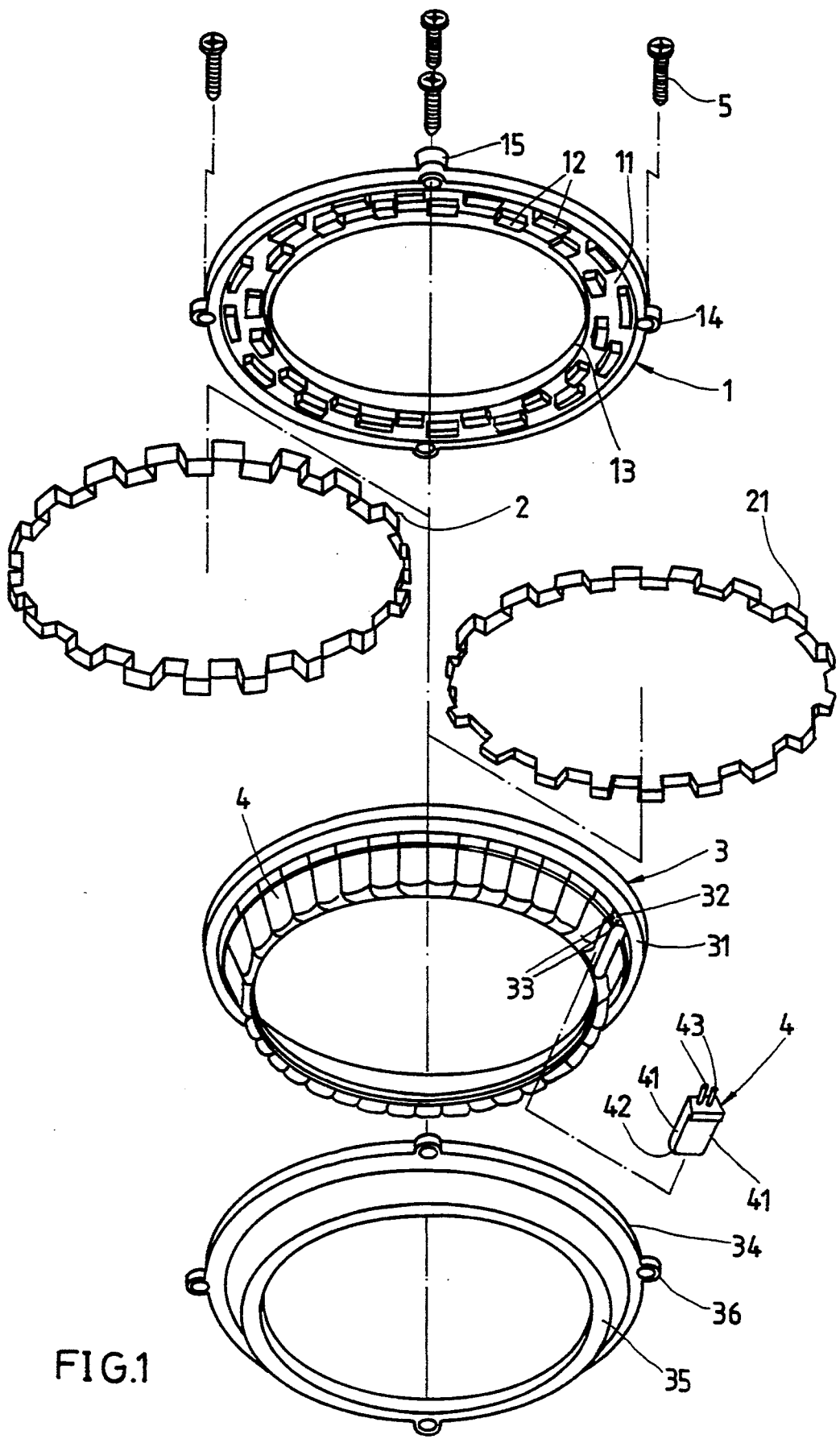
FIG. 1 is an exploded view of the apparatus of the present invention.
Figure 2:
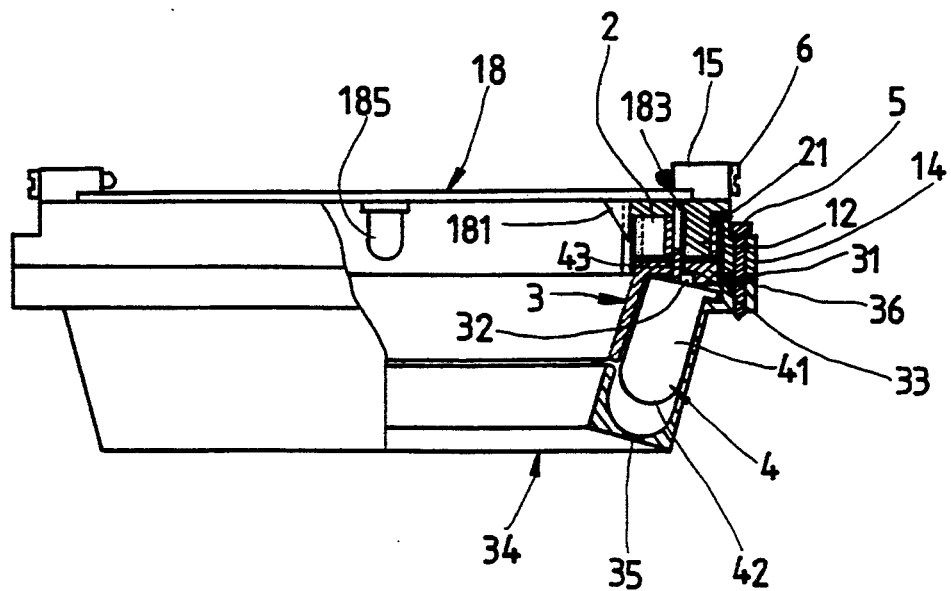
FIG. 2 is a sectional view of the apparatus of the present invention.

Referring to FIGS. 1 through 4, the apparatus in accordance with the present invention comprises mainly an annular mounting frame 1, two contact metal rings 2 and 21, an annular light holder 3, and a lens grip 34. The annular mounting frame 1 comprises two series of blocks 12 alternatively and concentrically disposed within an annular bottom groove 11 thereof to hold the contact metal rings 2 and 21 respectively permitting the contact metal rings 2 and 21 to be respectively connected to the positive and negative terminals of an electric power supply circuit, a plurality of vertical mounting lugs 14 spaced around the periphery, and a plurality of horizontal mounting lugs 15 spaced at the top. The annular light holder 3 comprises a mounting flange 31 around the border thereof at the top, which fits into the annular bottom groove 11 of the mounting frame 1 to hold down the contact metal rings 2 and 21, an annular groove 32 around the mounting flange 31 at the bottom, a plurality of mounting holes 33 closely spaced along the annular groove 32. There are light emitting diodes 4 are respectively fastened to the mounting holes 33. The lens grip 34 holds a lens 35 on the inside, having a plurality of mounting lugs 36 respectively connected to the vertical mounting lugs 14 on the mounting frame 1 by screws 5. Furthermore, the lens grip 34 is made gradually smaller toward the bottom so that light can be well condensed. The light emitting diodes 4 have each two opposite lateral walls 41 sloping downwards so that they can be abutted against one another. Furthermore, the two opposite ends of each light emitting diodes 4 are connected to the contact metal rings 2 and 21 by conductors 43. By means of the horizontal mounting lugs 15, the mounting frame 1 can be fastened to the bottom end of the microscope barrel 7 of a refracting unit by screws tightening up screws 6.

Referring to FIG. 4 again, there is a centering device 8 fastened to the annular mounting frame 1 at the top. The centering device 8 comprises two locating rods 181 and 182 at two opposite ends thereof respectively engaged into two opposite notches 16 on the annular mounting frame 1, two contact pins 183 and 184 inserted through a respective through hole 17 on the annular mounting frame 1 to make a respective electric contact with either contact metal ring 2 or 12, and a light emitting diode 185 disposed at the center of the annular mounting frame 1 and having two opposite ends respectively connected to the contact pins 183 and 184 by conductors (not shown).

Figure 3A:
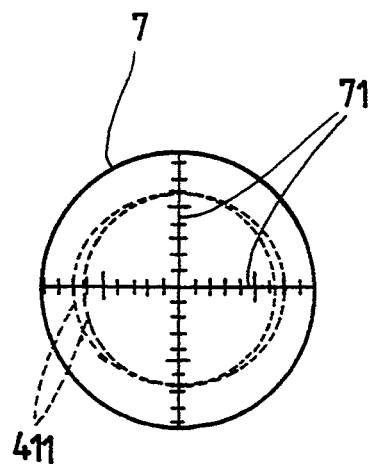
FIG. 3A shows the reading of the length of the X-axis and Y-axis of the spherical surface of the cornea.
Figure 3:
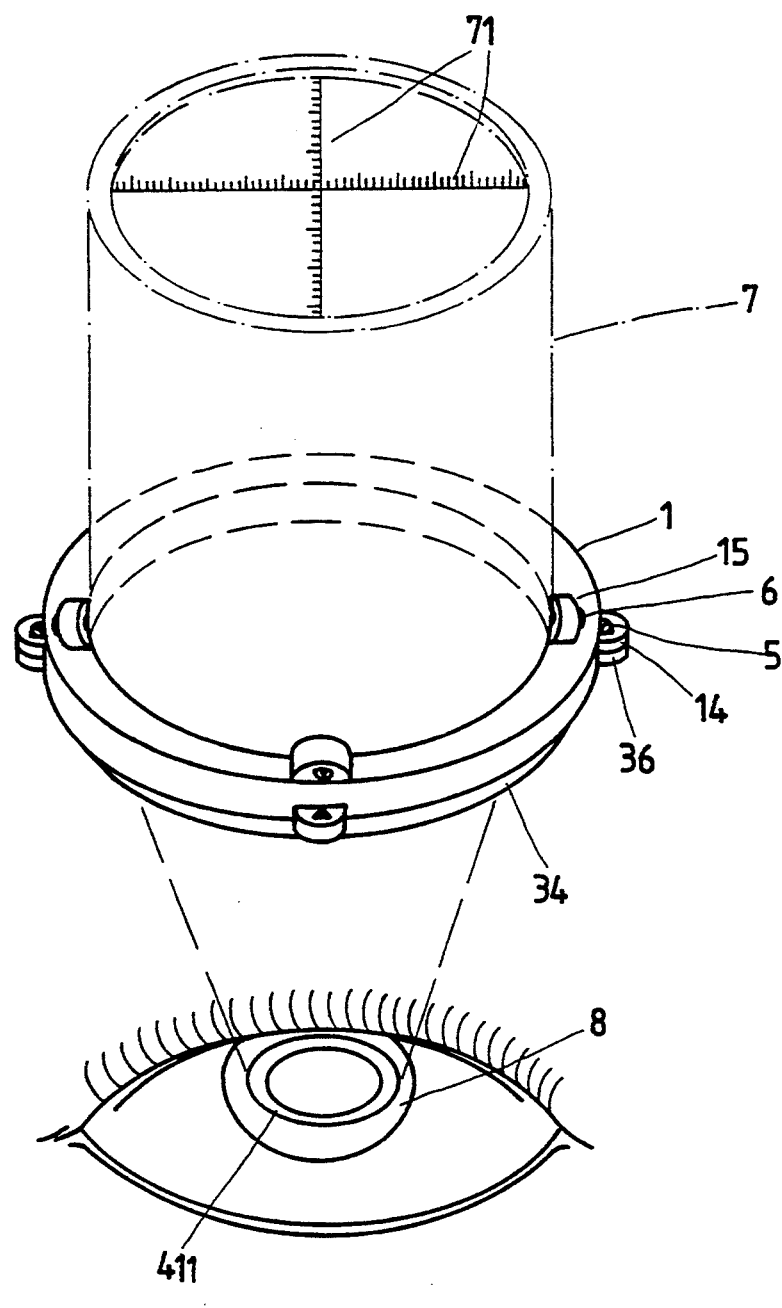
FIG. 3 shows the apparatus of the present invention coupled to the microscope barrel of a refracting unit and a ring of light projected by the apparatus onto the cornea.
Figure 4:
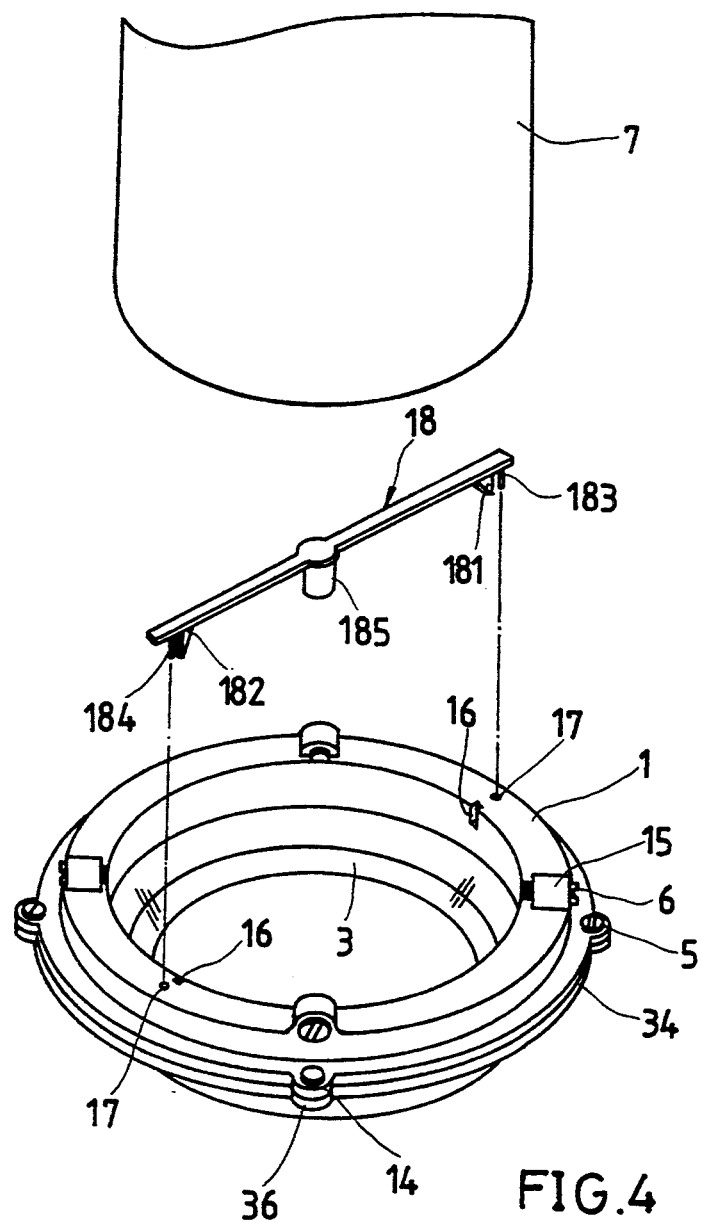
FIG. 4 is a dismantled view of the apparatus of the present invention, the centering device, and the microscope barrel.

Referring to FIGS. 3 and 3a, when the light emitting diodes 4 are turned on to project light, a ring of light 411 is projected on the the cornea 8 by the light emitting diodes 4, and therefore the examiner can read the length of the X-axis as well as Y-axis of the spherical surface of the cornea through the scale 71 on the microscope barrel 7. The annular light holder 3 and the lens grip 34 are respectively made of opaque material so that light from the light emitting diodes 4 can be focused onto the cornea.

Figure 5:
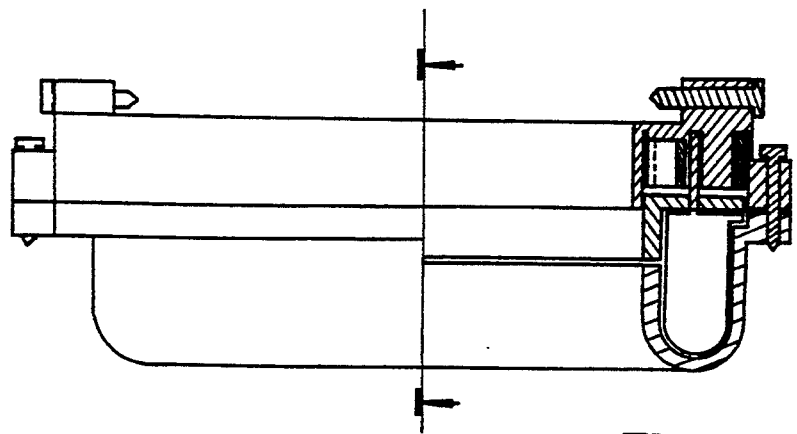
FIG. 5 shows an alternate form of the lens grip according to the present invention.

Referring to FIG. 5, as an alternate form of the present invention, the lens grip 35 may be made having a uniform inner diameter so that the light emitting diodes 4 are held in vertical and abutted one against one another.

What is claimed is:

1. An apparatus for measuring the spherical surface of the cornea comprising:

an annular mounting frame for fastening to the microscope barrel of a refracting unit, said annular mounting frame comprising two series of blocks alternatively and concentrically disposed within an annular bottom groove thereof, two contact metal rings respectively fastened to said series of blocks and connected to an electric power supply circuit thereof, a plurality of vertical mounting lugs spaced around the periphery, a plurality of horizontal mounting lugs spaced around a center opening thereof for fastening to the bottom end of the microscope barrel of a refracting unit by tightening up screws, two opposite notches, and two opposite through holes at the top;

a centering device having two locating rods at two opposite ends thereof respectively engaged into the two opposite notches on said annular mounting frame, two contact pins respectively inserted through the through hole on said annular mounting frame to make a respective electric contact with either contact metal ring, and a light emitting diode disposed at the center and having two opposite terminals respectively connected to said contact pins by a respective conductor;

an annular light holder fastened to said annular mounting frame, said annular light holder comprising a mounting flange fitted into the annular groove on said annular mounting frame, a plurality of mounting holes spaced along an annular groove thereof at the bottom, and a plurality of light emitting diodes respectively fastened to said mounting holes and abutted against one another and having each two opposite terminals respectively connected to said contact metal rings by a respective conductor; and a lens grip fastened to said annular mounting frame at the bottom to hold down said annular light holder, said lens grip comprising a lens on the inside for condensing the light of the light emitting diodes of said annular light holder into a ring of light for projecting onto the spherical surface of the cornea for measuring refraction of the eye.

* * * * *